US009750812B2

(12) United States Patent
Ali et al.

(10) Patent No.: US 9,750,812 B2
(45) Date of Patent: Sep. 5, 2017

(54) LIPID BASED PHARMACEUTICAL PREPARATIONS FOR ORAL AND TOPICAL APPLICATION; THEIR COMPOSITIONS, METHODS, AND USES THEREOF

(75) Inventors: Shoukath M. Ali, Waukegan, IL (US); Ateeq Ahmad, Wadsworth, IL (US); Moghis U. Ahmad, Wadsworth, IL (US); Saifuddin Sheikh, Waukegan, IL (US); Imran Ahmad, Wadsworth, IL (US)

(73) Assignee: JINA PHARMACEUTICALS, INC., Libertyville, IL (US)

( * ) Notice: Subject to any disclaimer, the term of this patent is extended or adjusted under 35 U.S.C. 154(b) by 1371 days.

(21) Appl. No.: 13/120,127

(22) PCT Filed: Sep. 25, 2009

(86) PCT No.: PCT/US2009/058463
§ 371 (c)(1),
(2), (4) Date: Apr. 28, 2011

(87) PCT Pub. No.: WO2010/036947
PCT Pub. Date: Apr. 1, 2010

(65) Prior Publication Data
US 2011/0212167 A1    Sep. 1, 2011

Related U.S. Application Data

(60) Provisional application No. 61/100,714, filed on Sep. 27, 2008.

(51) Int. Cl.
| | |
|---|---|
| A61K 47/24 | (2006.01) |
| A61K 9/127 | (2006.01) |
| A61K 8/04 | (2006.01) |
| A61K 9/00 | (2006.01) |
| A61K 9/08 | (2006.01) |
| A61K 9/10 | (2006.01) |
| A61K 31/506 | (2006.01) |
| A61K 31/58 | (2006.01) |
| A61K 45/06 | (2006.01) |
| A61K 47/44 | (2017.01) |

(52) U.S. Cl.
CPC ............ *A61K 47/24* (2013.01); *A61K 9/0014* (2013.01); *A61K 9/08* (2013.01); *A61K 9/10* (2013.01); *A61K 31/506* (2013.01); *A61K 31/58* (2013.01); *A61K 45/06* (2013.01); *A61K 47/44* (2013.01)

(58) Field of Classification Search
USPC ......................................................... 424/450
See application file for complete search history.

(56) References Cited

U.S. PATENT DOCUMENTS

| | | | |
|---|---|---|---|
| 4,663,167 A | 5/1987 | Lopez-Berestein et al. | |
| 4,761,288 A * | 8/1988 | Mezei ............................ | 424/450 |
| 4,828,837 A * | 5/1989 | Uster et al. .................... | 424/450 |
| 5,000,887 A * | 3/1991 | Tenzel et al. .................. | 264/4.6 |
| 5,030,442 A | 7/1991 | Uster et al. | |
| 5,053,217 A * | 10/1991 | Lehigh ............................ | 424/45 |
| 5,540,934 A * | 7/1996 | Touitou .......................... | 424/450 |
| 5,616,334 A | 4/1997 | Janoff et al. | |
| 6,001,812 A * | 12/1999 | Mahe ............................. | 514/10.7 |
| 6,284,234 B1 | 9/2001 | Niemiec et al. | |
| 6,406,713 B1 | 6/2002 | Janoff et al. | |
| 6,596,266 B2 * | 7/2003 | Catalfo et al. .................. | 424/74 |
| 6,656,460 B2 | 12/2003 | Benita et al. | |
| 6,733,776 B1 | 5/2004 | Li et al. | |
| 6,984,397 B2 * | 1/2006 | Fujisaki et al. ................ | 424/450 |
| 7,053,061 B2 * | 5/2006 | Pai et al. ........................ | 514/31 |
| 2002/0102295 A1 | 8/2002 | Niemiec et al. | |
| 2003/0039613 A1 * | 2/2003 | Unger et al. ................... | 424/9.51 |
| 2003/0108626 A1 | 6/2003 | Benita et al. | |
| 2004/0175417 A1 | 9/2004 | Proffitt et al. | |
| 2004/0205910 A1 | 10/2004 | Li et al. | |
| 2005/0232984 A1 * | 10/2005 | Haas et al. ..................... | 424/450 |
| 2006/0034906 A1 * | 2/2006 | Boni et al. ..................... | 424/450 |
| 2006/0105968 A1 * | 5/2006 | Cleary et al. .................. | 514/28 |
| 2007/0237750 A1 * | 10/2007 | Naughton ...................... | 424/93.7 |
| 2008/0248117 A1 * | 10/2008 | Kolter et al. ................... | 424/486 |

FOREIGN PATENT DOCUMENTS

| | | |
|---|---|---|
| CN | 101559038 | 3/2011 |
| EP | 0177223 A2 | 4/1985 |

(Continued)

OTHER PUBLICATIONS

European Search Report for EP Patent Application 09816940.2, mailed Nov. 30, 2012, 7 pages.

(Continued)

*Primary Examiner* — Gollamudi Kishore
(74) *Attorney, Agent, or Firm* — Casimir Jones, S.C.; Mary Ann Brow

(57) ABSTRACT

The present invention relates to the topical and oral delivery of a composition comprising one or more active agents for treating a disease or symptoms in a subject. In some embodiments, the present invention comprises a composition comprising at least one active compound, e.g., finasteride or minoxidil, and one or more lipids. In some embodiments, the present invention relates to composition and method of preparation for treating androgenic alopecia (AGA), prevention of hair loss and female hirsutism. In some embodiment, the present invention comprises finasteride and at least one lipid component for the treatment of benign prostatic hyperplasia. In some embodiment, the present invention comprises tacrolimus or amphotericin B and at least one lipid component for the treatment of skin or eye related diseases. The present invention provides a method of preparation of a composition comprising at least one active compound and at least one lipid and administering the composition to a subject by oral or topical delivery. In certain embodiments the subject is a mammal. In certain preferred embodiment, the subject is human.

12 Claims, No Drawings

(56) References Cited

FOREIGN PATENT DOCUMENTS

| | | |
|---|---|---|
| EP | 0285382 B1 | 4/1994 |
| EP | 1060732 | 12/2000 |
| EP | 1080730 | 3/2001 |
| EP | 1273299 | 1/2003 |
| GB | 2256139 | 12/1992 |
| JP | 61-85312 A | 4/1986 |
| JP | H09-71513 | 3/1997 |
| JP | 10-59829 A | 3/1998 |
| JP | 2001288090 | 10/2001 |
| JP | 2002308740 | 10/2002 |
| JP | 2003-521452 A | 7/2003 |
| JP | 2003521452 | 7/2003 |
| JP | 2004-538243 | 12/2004 |
| JP | 2006-514044 | 4/2006 |
| JP | 2008-520547 | 6/2008 |
| WO | WO89/05636 | 6/1989 |
| WO | WO90/11780 | 10/1990 |
| WO | 92/03123 | 3/1992 |
| WO | 97/12602 | 10/1997 |
| WO | 99/61059 | 12/1999 |
| WO | WO00/07627 | 2/2000 |
| WO | 01/85142 | 11/2001 |
| WO | 02/07728 | 1/2002 |
| WO | 03/013245 | 2/2003 |
| WO | 2004/060344 | 7/2004 |
| WO | WO2005/000266 | 1/2005 |
| WO | 2006/041942 | 4/2006 |
| WO | 2008/038140 | 4/2008 |
| WO | WO2008/127358 | 10/2008 |

OTHER PUBLICATIONS

Deray et al., "Nephrotoxicite de l'amphotericine B," Nephrologie, 2002, 23(3):119-122.

Hammarstrom and Smith, "In Vitro Activating Properties of Polyene Antibotics for Murine Lymphocytes," Acta Patho. Microbial. Scand., 1977, 85C(4):277-283.

Medoff and Kobayashi, "Amphotericin B: Old Drug, New Therapy," JAMA, 1975, 232(6):619-620.

Olsen et al., "Topical minoxidil in early male pattern baldness," Journal of the American Academy of Dermatology, 1985, 13:185-192.

Remington's Pharmaceutical Sciences, 15th Edition, 1975, Mack Publishing Company, Easton, PA (TOC Only will provide specific pages upon examiner request).

Roberts, "Androgenetic alopecia: Treatment results with topical minoxidil," Journal of the American Academy of Dermatology,1987, 16:705-710.

Roberts, "Androgenetic Alopecia in Men and Women: An Overview of Cause and Treatment," Dermatology Nursing, 1997, 9(6):379-386.

Valeriote et al., "Protective Effects of Amphotericin B Against Spontaneous and Transplantable Murine Tumors," Journal of the National Cancer Institute, 1976, 56(3):557-560.

English Abstract of Deray et al., "Nephrotoxicite de l'amphotericine B," Nephrologie, 2002, 23(3):119-122 (1 page).

English Abstract of JP10-59829 (1 page).

EP0177223 is the English equivalent of JP61-85312.

U.S. Pat. No. 6,284,234, issued Sep. 4, 2001, is the English language equivalent of JP2003521452.

EP Publication 1273299, published Jan. 8, 2003, is the English language equivalent of JP2001288090.

EP Publication 1080730, published Mar. 7, 2001, is the English language equivalent of WO 99/61059.

English Abstract of JP2002308740, retrieved Feb. 20, 2014, 1 page.

Sekine et al., New Cosmetics Handbook, Nikko Chemicals, Oct. 30, 2006, pp. 277-282.

\* cited by examiner

US 9,750,812 B2

LIPID BASED PHARMACEUTICAL PREPARATIONS FOR ORAL AND TOPICAL APPLICATION; THEIR COMPOSITIONS, METHODS, AND USES THEREOF

This application is a §371 US National Entry of International Application No. PCT/US2009/058463, filed Sep. 25, 2009, which claims the benefit of U.S. Provisional Application No. 61/100,714, filed Sep. 27, 2008, each of which is incorporated herein by reference in their entireties.

FIELD OF THE INVENTION

The invention relates to compositions comprising active components or compounds, e.g., pharmaceutical compounds, and lipids, including, e.g., solutions, complexes, micelles, emulsions, liposomes or lipidic particle, and mixture of micelles and vesicles. The invention further relates to their methods of preparation, and uses in the treatment of diseases. The invention also relates to a method for the topical delivery of active agents, and compositions used therein. In some embodiments, the invention relates to compositions comprising, hair loss preventing or hair growth drugs such as finasteride and minoxidil. In some embodiments, the invention relates to composition comprising active compounds for use in treating skin or eye infections, or diseases related to skin or eyes, e.g., in mammals. In some embodiments, the invention also related to a method for the oral delivery of active agents. Methods according to the present invention are suitable for practice on an industrial manufacturing scale, and may be practiced, e.g., as a continuous process.

BACKGROUND OF THE INVENTION

Androgenic alopecia (AGA) is the most common form of hair loss, affecting approximately 30 to 40 percent of adult men and women. The incidence is generally considered to be greater in males than females. In men, the condition is also called male-pattern baldness. Commonly treatments for androgenic alopecia include hair follicle transplants, topical therapies, and orally prescribed antiandrogens (J. L. Roberts, 1997). The hyperandrogenic stimulation that causes alopecia also produces other undesirable physiological symptoms including acne vulgaris, benign prostatic hyperplasia, female hirsutism, and seborrhea.

Early attempts to provide a chemotherapeutic agent to counter the undesirable results of hyperandrogeneticity resulted in the discovery of several steroidal antiandrogens having undesirable hormonal activities of their own. The principal mediator of androgenic activity in some target organs, e.g. the prostate, is 5α-dihydrotestosterone (DHT), formed locally in the target organ by the action of testosterone-5-α-reductase. Inhibitors of testosterone-5α-reductase will serve to prevent or lessen symptoms of hyperandrogenic stimulation in these organs (Gormley et al. U.S. Pat. No. 5,981,543, 1999 and Rasmusson et al. U.S. Pat. No. 4,377,584, 1983).

Minoxidil (6-(1-piperidinyl)-2,4-pyrimidinediamide 3 oxide) is a drug known for the treatment of AGA. Minoxidil is effective when delivered topically ar a concentration of about 0.01% to about 5%. The topical solution of Minoxidil is currently marketed as "Rogaine" having 2% minoxidil concentration in a solution of (60% v/v) propylene glycol, and water. Disadvantageously, clinical trials have shown that the topical application of a 2% monixidil solution to patients experiencing hair loss results stimulated dense hair regrowth in only less than about 5% of the patients and moderate hair regrowth in only about 30% of the patients (E. A. Olsen, et al., 1985; J. Roberts, 1987), S. Niemiee et al. U.S. Pat. No. 6,419,913 B1, 2002).

Finasteride is a synthetic androgen inhibitor currently marketed as PROSCAR® for the treatment of benign prostatic hyperplasia. It has also been marketed orally in low dosage form as PROPECIA® for the treatment of androgenic alopecia (AGA) (hair loss). Chemically, finasteride is (5α, 17β)-N-(1,1-dimethylethyl)-3-oxo-4-azaandrost-1-ene-17-carboxamide and is practically insoluble in water, and is soluble only in organic solvents such as ethanol and methanol. Finasteride is known to inhibit 5α-reductase type 2.

Although, finasteride is currently administered orally, it is not available topically as approved product for the treatment of AGA. The side effects as a result of the oral administration for finasteride include erectile dysfunction, impotence, low libido, gynecomestica, and facial hair growth.

Development of new lipid-based formulation is needed to improve oral and or transdermal delivery and reduce the toxicity associated with compositions such as finasteride and minoxidil.

SUMMARY OF THE INVENTION

The present invention relates to a new methods of preparing lipid formulations of active compounds, and methods of using the formulation in treating a disease or symptom in a subject. In some embodiments, the present invention comprises a composition comprising at least one active agent, such as finasteride or minoxidil. In some embodiments, the present invention comprises a method comprising preparing a composition comprising at least one active compound, e.g., finasteride, and one or more lipids and administering the composition to a subject. In certain embodiments the subject is a mammal. In certain preferred embodiments, the subject is human.

Another objective of the present invention is to provide lipid formulations comprising at least one active component and at least one lipid, e.g., a phospholipid, or neutral lipid formed in a suitable vehicle. The suitable vehicle in the present invention comprises a non-toxic solvent or an aqueous medium.

The amount of phospholipid included in a composition according to the present invention is not limited to any particular amount or percentage (e.g., by weight) of the final composition. In some embodiments, the proportion of at least one phospholipid is between about 0.5% to about 98% of total lipids (e.g., a commercially usable form) by weight. In some preferred embodiments, the amount of the at least one phospholipid is in between 0.5% to 90% of the lipid complex by weight.

A lipid formulation of the present invention is not limited to any particular use or application. For example, a lipid formulation of an active component according to the present invention comprising a pharmaceutically active ingredient can be used for different pharmaceutical applications. An aqueous system or a non-toxic solvent system of the present invention can also be used in the formation of unloaded lipid complexes (e.g., without any encapsulated active ingredient) for use, e.g., as controls for complexes comprising active components.

As for example, it is possible to encapsulate or entrap finasteride, in the inventive liposome system. Such a pharmaceutical product is particularly suitable for oral or topical application. Furthermore, the known active ingredients are for the treatment of benign prostatic hyperplasia, androgenic alopecia (male and female baldness), and prevention of hair loss, female hirsutism, acne vulgaris and seborrhea.

In some embodiments, the one or more lipids of a composition according to the present invention comprise one or more cholesterol, cholesteryl sulfate and its salts (e.g., sodium salt), cholesteryl hemisuccinate, cholesteryl succinate, cholesteryl oleate, polyethylene glycol derivatives of cholesterol (cholesterol-PEG), coprostanol, cholestanol, cholestane, cholic acid, cortisol, corticosterone, hydrocortisone, or calciferol, while in some embodiments, the one or more lipids comprises a sterol. In certain embodiments, the sterol is β-sitosterol, stigmasterol, stigmastanol, lanosterol, α-spinasterol, lathosterol, campesterol or a mixture thereof. In some embodiments, the sterol is guggulsterol, derivatives of guggulsterol (e.g., guggulsulfate and its salt such as sodium salt, guggulmyristate, gugullaurate, gugguloleate, or short chain fatty acid derivatives of guggulsterol or mixture thereof.

In some embodiments, the one or more lipids of a composition according to the present invention comprises one or more of fatty acids having a chain length of about $C_4$-$C_{34}$. In some embodiments, one or more fatty acid chains are unsaturated, while in some embodiments, one or more of the fatty acid chains are saturated. In some embodiments, one or more of the fatty acids are in salt form, while in some embodiments; one or more of the fatty acids are in acidic form. In some embodiments, one or more fatty acids are in the form of an ester.

In some embodiments, the one or more lipids of a composition according to the present invention comprises one or more of long alkyl chain alcohols having a chain length of about $C_4$-$C_{34}$. In some embodiments, one or more alkyl chains are unsaturated, while in some embodiments, one or more of the alkyl chains are saturated.

In some embodiments, one or more lipids of a composition according to the present invention comprise a phospholipid. In some preferred embodiments, one or more of the lipids of the composition comprises a phosphatidylcholine or phosphatidylglycerol, while in some preferred embodiments; one or more of the lipids of the composition comprises a phosphatidylethanolamine, phosphatidylserine, phosphatidylinositol, or phosphatidic acid. In some preferred embodiments, one or more lipids of the present invention comprise a soybean phospholipid. In some particularly preferred embodiments, a soybean phospholipid used in the methods and compositions of the present invention comprises a large concentration of phosphatidylcholine. In still more particularly preferred embodiments, a soybean phospholipid used in the methods and compositions of the present invention contains at least 90% by weight phosphatidylcholine. In some embodiments, one or more phospholipids are pegylated (PEG) derivatives of phospholipids. In certain embodiments, one or more of the lipids of the composition comprise a pegylated derivative of a distearoylphosphatidylglycerol, a dimyristoylphosphatidylglycerol, or a dioleoylphosphatidylglycerol phospholipid.

In some embodiments, one or more lipids of a composition according to the present invention comprise a monoglyceride, a diglyceride, or a triglyceride lipid.

The method of composition, wherein said fatty acids of mono-, di-, and triglycerides are selected from a group of saturated and unsaturated fatty acids having short chain or long chain.

In some embodiments, a composition according to the present invention further comprises polyethylene glycol (PEG). In some embodiments, the PEG has an average molecular weight ranging from 200-20,000, while in certain preferred embodiments, the average molecular weight of the PEG is in between 500-2000.

In some embodiments, a composition according to the present invention comprises active compound (for example finasteride), cholesterol or cholesterol derivatives and one or more phospholipids. In some embodiments in which the composition comprises a cholesterol derivative, the cholesterol derivative is cholesteryl sulfate. In some embodiments wherein the phospholipid comprises soy phosphatidylcholine or hydrogenated phosphatidylcholine. In some preferred embodiments, the mole ratio of active compound (for example, finasteride) and cholesterol or cholesterol derivative is in the range of about 1:0.5 and 1:50, while in certain particularly preferred embodiments, the mole ratio of active compound (for example, finasteride) and cholesterol or cholesterol derivative is in between about 1:1 and 1:10.

In some embodiments, one or more lipids of a composition according to the present invention comprise hydrogenated soy phosphatidylcholine, wherein the mole ratio of active compound (for example, finasteride) and hydrogenated soy phosphatidylcholine is in between about 1:1 and 1:80. In certain preferred embodiments, the mole ratio of active compound (for example, finasteride) and hydrogenated soy phosphatidylcholine is in between about 1:1 and 1:60.

In some embodiments, one or more lipids of a composition according to the present invention comprise soy phosphatidylcholine, wherein the mole ratio of active compound (for example, finasteride) and soy phosphatidylcholine is in between about 1:1 and 1:80. In certain preferred embodiments, the mole ratio of active compound (for example, finasteride) and soy phosphatidylcholine is in between about 1:1 and 1:60.

In some embodiments, a composition according to the present invention comprises active compound (for example, finasteride,) at a concentration of from about 0.5 mg/mL to about 200 mg/mL while in some preferred embodiments, the active compound (for example, finasteride) of the composition is at a concentration of from about 1 mg/mL to about 10 mg/mL. In some particularly preferred embodiments, the composition of the invention comprises active compound (for example, finasteride) is at a concentration of about 1 mg/mL to about 5 mg/mL.

In some embodiments, a composition according to the present invention comprises active compound (for example, finasteride,) at a concentration of from about 0.5 mg/g to about 200 mg/g while in some preferred embodiments, the active compound (for example, finasteride) of the composition is at a concentration of from about 1 mg/g to about 50 mg/g. In some particularly preferred embodiments, the composition of the invention comprises active compound (for example, finasteride) is at a concentration of about 1 mg/g to about 10 mg/g.

In some embodiments, a composition according to the present invention comprises a total lipid concentration or proportion of from about 0.5% by weight to about 95% by weight, while in some preferred embodiments; the composition comprises a total lipid concentration of from about 0.5% by weight to about 80% by weight. In certain particularly preferred embodiments, the composition comprises a total lipid concentration of from about 10% by weight to about 90% by weight.

In some embodiments, a composition according to the present invention comprises active compound (for example, finasteride) and total lipid(s) having a weight-to-weight ratio ranging from about 1:1 to about 1:100, while in certain preferred embodiments, the ratio is in between 1:1 to about 1:60.

In some embodiments, a composition according to the present invention comprises a composition selected from the group consisting of a micelle and an emulsion. In certain preferred embodiments, the composition comprises a plurality of micelles, wherein said micelles are in the form of monomeric, dimeric, polymeric or mixed micelles.

The present invention is not limited to any particular form of composition of the invention. For example, in some embodiments, a composition according to the present invention is in a lyophilized form. In some, embodiments, the composition further comprise a cryoprotectant. In certain, preferred embodiments, the cryoprotectant comprise one or more sugars, while in particularly preferred embodiments; the one or more sugars comprise trehalose, maltose, lactose, sucrose, glucose, and/or dextran.

In some embodiments, a composition according to the present invention comprises complexes, liposomes, micelles, vesicles that have a diameter of about 20 microns or less, while in some embodiments, the complexes, liposomes, micelles, vesicles that have a diameter of about 10 microns or less. In some embodiments, the complexes, liposomes, micelles, vesicles that have a diameter of about 5 microns or less, while in some embodiments, the complexes, liposomes, micelles, vesicles that have a diameter of about 1 micron or less. In some embodiments, the complexes, liposomes, micelles, vesicles that have a diameter of about 500 nm or less, while in some embodiments, the complexes, liposomes, micelles, vesicles that have a diameter of about 200 nm or less. In some preferred embodiments, the complexes, liposomes, micelles, vesicles that have a diameter of about 100 nm or less.

In some embodiments, a composition according to the present invention is in a powder form, while in some embodiments, the complex is in a solution form. In some embodiments, the composition is in a suspension form, while in other embodiments, the composition is in an emulsion form, while in still other embodiments, the composition is in a micelle form or mixed micellar form or in a liposome form. In some embodiments, the composition is in a lyophilized or gel form, while in some embodiments, the composition is in a paste form. In some embodiments, the composition is a mixture of mixed micelles, liposomes or vesicles form.

The composition produced according to the present inventive method can be filled directly in corresponding ampoules, vials, bottles, tubes in a condition ready to use. The product can be lyophilized, if desired to provide the composition in powder form, which can be mixed in a suitable vehicle for topical application. Examples of suitable vehicles include but not limited to oil, gel, paste, lotion, shampoo, soap, and the like. In some embodiments, the lyophilized powder can be used for oral delivery of therapeutic agent (for example, finasteride).

It is contemplated that the methods and compositions of the present invention are used to treat androgenic alopecia such as male and female baldness, prevention of hair loss, female hirsutism, acne vulgaris, and seborrhea. In some embodiments, the present invention comprises use of the compositions described above in the preparation of a medicament for treatment of a subject for, e.g., androgenic alopecia such as male and female baldness, prevention of hair loss, female hirsutism, acne vulgaris, and seborrhea.

It is contemplated that in some embodiments, the exposing of a cell in a subject comprises topical delivery of the composition to the subject. In some preferred embodiments, the subject is a mammal. In some particularly preferred embodiments, the mammal is human.

DEFINITIONS

The term "lipid composition" as used herein refers to amphoteric compounds which are capable of liposome formation, vesicle formation, micelle formation, emulsion formation, and are substantially non-toxic when administrated at the necessary concentrations as liposomes. The lipid composition may include without limitation egg phosphatidylcholine (EPC), egg phosphatidylglycerol (EPG), soy phosphatidylcholine (SPC), hydrogenated soy phosphatidylcholine (HSPC), dimyristoylphosphatidylcholine (DMPC), dimyristoylphosphatidylglycerol (DMPG), Dipalmitoylphosohatidylcholine (DPPC), disteroylphosphatidylglycerol (DSPG), dipalmitoylphosphatidylglycerol (DMPG), cholesterol (Chol), cholesterol sulfate and its salts (CS), cholesterol hemisuccinate and its salts (Chems), cholesterol phosphate and its salts (CP), cholesterylphospholine and other hydroxycholesterol or amino cholesterol derivatives, guggulsterol or guggulsterol derivatives, e.g., guggulsulfate and its salts, guggullaurate, guggulmyristate or other saturated or unsaturated fatty acid derivatives of guggulsterol.

As used herein, the term "aqueous" as used in reference to a solvent, fluid, or system, refers to a water-based solvent, fluid or system that does not contain any organic solvents. The aqueous system may further contain buffer(s). Examples of base or buffer includes but not limited to sodium succinate dibasic, sodium acetate, sodium phosphate monobasic, sodium phosphate dibasic, sodium phosphate tribasic, sodium citrate, sodium hydroxide, and the like.

As used herein, the term "non-toxic solvent" refers to alcohols, and oils. Examples of alcohols include but not limited to ethanol, 1-propanol, isopropyl alcohol, propylene glycol, butanol, and t-butanol. Suitable examples of oils include but not limited to olive oil, soybean oil, coconut oil, almond oil, sunflower oil, sun flower oil, vegetable oil, canola oil, coconut oil, sesame seed oil, avocado oil, cod oil and the like.

The term "encapsulating amount" or "entraping amount" refers to the amount of lipid necessary to encapsulate or entrap the poorly soluble compound and form liposome or lipidic particles of appropriate mean particle size less than 5,000 nm in diameter, preferably between 30-1000 nm. The encapsulating amount will depend on the pharmaceutically active compounds and process conditions selected, but in general range in between from 2:1 to about 1:100 compound: lipid ratio; preferably about 1:1 to about 1:50.

The term "lipidic particle" as used herein refers to particles of undefined structure which consist of a suitable lipid and an encapsulated or complexed pharmaceutically active compound. Lipidic particles may have a lamellar structure but are not required to exhibit any defined structure.

As used herein, the term "effective amount" refers to the amount of an active composition (e.g., a pharmaceutical compound or composition provided as a component in a lipid formulation) sufficient to effect beneficial or desired results.

An effective amount can be administered in one or more administrations, applications or dosages and is not intended to be limited to a particular formulation or administration route.

As used herein, the terms "active" or "pharmaceutically active" as used in reference to an agent, composition, or compound, refers to an agent that, upon administration or application, causes a beneficial, desired, or expected result. The administration may be in one or more administrations, applications or dosages and is not intended to be limited to a particular formulation or administration route. The term is not limited to any particular level of activity. For example, a lipid formulation of an active agent need not have the same level of activity as a different formulation of an active agent, so long as the active agent in the lipid formulation is sufficiently active that an effective amount of the active agent can be administered by administration of the lipid formulation of the agent.

The terms "agent" and "compound" are used herein interchangeably to refer to any atom, molecule, mixture, or more complex composition having an attributed feature. For example, an "active agent" or "active compound" refers to any atom, molecule, preparation, mixture, etc., that, upon administration or application, causes a beneficial, desired, or expected result.

As used herein, the term "administration" refers to the act of giving a drug, prodrug, or other active agent, or therapeutic treatment (e.g., compositions of the present invention) to a subject. Exemplary routes of administration to the human body can be through mouth and through skin. Administration may be in one or more administrations, applications or dosages, and is not intended to be limited to a particular administration route.

As used herein, the term "co-administration" refers to the administration of at least two agent(s) (e.g., two separate lipid compositions, containing different active compounds) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., an active pharmaceutical compound) with a carrier, inert or active (e.g., a phospholipid), making the composition especially suitable for diagnostic or topical therapeutic use.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to non-toxic solvent, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be formulated for horticultural or agricultural use. Such formulations include dips, sprays, seed dressings, stem injections, sprays, and mists.

As used herein, the term "pharmaceutically acceptable salt" refers to any salt (e.g., obtained by reaction with an acid or a base) of a compound of the present invention that is physiologically tolerated in the target subject (e.g., a mammalian subject). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenyl propionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "Polyethylene glycol (PEG)" includes polymers of lower alkylene oxide, in particular ethylene oxide (polyethylene glycols) having an esterifiable hydroxyl group at least at one end of the polymer molecule, as well as derivatives of such polymers having esterifiable carboxyl groups. Polyethylene glycols of an average molecular weight ranging from 200-20,000 are preferred; those having an average molecular weight ranging from 500-2000 are particularly preferred.

The use of terms "a" and "an" and "the" and similar referents in the context of describing the invention (especially in the context of the following claims) are to be construed to cover both the singular and the plural, unless otherwise indicated herein or clearly contradicted by context. The terms "comprising", "including", "having", and "containing" are to be construed as open-ended terms (i.e. meaning "including but not limited to") unless otherwise noted. The use of any and all examples, or exemplary language (e.g., "such as") provided herein, is intended merely to better illuminate the invention and does not pose a limitation on the scope of the invention unless otherwise claimed. No language in the specifications should be constructed as indicating any non-claimed element as essential to the practice of the invention.

DETAILED DESCRIPTION OF THE INVENTION

This invention relates to the preparation of a solution, suspension, liposomes, lipid complex, or micelles in an aqueous or a non-toxic solvent system. The inventive preparation involves at least one phospholipid such as Soy phosphatidylcholine in aqueous media or in a non-toxic solvent with therapeutically active insoluble or poorly soluble compounds.

Particular embodiments of the invention are described in the Summary, and in this Detailed Description of the Invention. Although the invention has been described in connection with specific embodiments, it should be understood that the invention as claimed should not be unduly limited to such specific embodiments. For example, the compositions and methods of the present invention are described in connection with particular hair growth agent, such as finasteride or minoxidil. It should be understood that the present invention is not limited to methods or compositions using or comprising finasteride or minoxidil.

In some embodiments, the present invention comprises a lipid composition with active compound (for example, finasteride) in which the composition contains lipid or a mixture of lipids. In some embodiments, the composition is in the form of solutions, micelles, emulsions or mixture of micelles and vesicles, gels, paste. The micelles of the present invention can be in the form, e.g., of monomeric, dimeric, polymeric or mixed micelles. In some embodiments, the composition including micelles, emulsions or mixture of micelles and vesicles are predominately in the size range of 50 nm-20 micron, while in some preferred embodiments, the micelles and emulsions are in the size range of 50 nm-5 micron.

In some embodiments, active agent-lipid composition (for example, finasteride-lipid composition contain cholesterol or cholesterol derivatives. Examples of cholesterol derivatives that find use in the present invention include but are not limited to cholesteryl sulfate, cholesteryl hemisuccinate, cholesteryl succinate, cholesteryl oleate, cholesteryl linoleate, cholesteryl eicosapentenoate, cholesteryl linolenate, cholesteryl arachidonate, cholesteryl palmitate, cholesteryl stearate, cholesteryl myristate, polyethylene glycol derivatives of cholesterol (cholesterol-PEG), water soluble cholesterol (for example, cholesterol methyl-β-cyclodextrin), coprostanol, cholestanol, or cholestane, cholic acid, cortisol, corticosterone or hydrocortisone and 7-dehydrocholesterol.

In some preferred embodiments, the compositions also include α-, β-, γ-tocopherols, vitamin E, calciferol, organic acid derivatives of α-, β-, γ-tocopherols, such as α-tocopherol hemisuccinate (THS), α-tocopherol succinate, or mixtures thereof.

In some preferred embodiments, active agent-lipid compositions (for example, finsteride-lipid composition) contain sterols. Examples of sterols that find use in the present invention include β-sitosterol, stigmasterol, stigmastanol, lanosterol, α-spinasterol, lathosterol, campesterol and/or mixtures thereof.

In some preferred embodiments, active agent-lipid composition (for example, finasteride-lipid composition) contain guggulsterol and guggulsterol derivatives such as, guggul sulfate and its salt (preferably sodium salt), guggullaurate and guggulsterol derivatives containing long chain or short chain, saturated or unsaturated fatty acids (such as gugguloleate).

Compositions of the present invention also include active compounds (for example, finasteride) with free and/or salts or esters of fatty acid. In some preferred embodiments, fatty acids range from carbon chain lengths of about $C_2$ to $C_{34}$, preferably between about $C_4$ and about $C_{24}$, and include tetranoic acid ($C_{4:0}$), pentanoic acid ($C_{5:0}$), hexanoic acid ($C_{6:0}$), heptanoic acid ($C_{7:0}$), octanoic acid ($C_{8:0}$), nonanoic acid ($C_{9:0}$), decanoic acid ($C_{10:0}$), undecanoic acid ($C_{11:0}$), dodecanoic acid ($C_{12:0}$), tridecanoic acid ($C_{13:0}$), tetradecanoic (myristic) acid ($C_{14:0}$), pentadecanoic acid ($C_{15:0}$), hexadecanoic (palmatic) acid ($C_{16:0}$), heptadecanoic acid ($C_{17:0}$), octadecanoic (stearic) acid ($C_{18:0}$), nonadecanoic acid ($C_{19:0}$), eicosanoic (arachidic) acid ($C_{20:0}$), heneicosanoic acid ($C_{21:0}$), docosanoic (behenic) acid ($C_{22:0}$), tricosanoic acid ($C_{23:0}$), tetracosanoic acid ($C_{24:0}$), 10-undecenoic acid ($C_{11:1}$), 11-dodecenoic acid ($C_{12:1}$), 12-tridecenoic acid ($C_{13:1}$), myristoleic acid ($C_{14:1}$), 10-pentadecenoic acid ($C_{15:1}$), palmitoleic acid ($C_{16:1}$), oleic acid ($C_{18:1}$), linoleic acid ($C_{18:2}$), linolenic acid ($C_{18:3}$), eicosenoic acid ($C_{20:1}$), eicosdienoic acid ($C_{20:2}$), eicosatrienoic acid ($C_{20:3}$), arachidonic acid (cis-5,8,11,14-eicosatetraenoic acid), and cis-5,8,11,14,17-eicosapentaenoic acid, among others. Other fatty acid chains also can be employed in the compositions. Examples of such include saturated fatty acids such as ethanoic (or acetic) acid, propanoic (or propionic) acid, butanoic (or butyric) acid, hexacosanoic (or cerotic) acid, octacosanoic (or montanic) acid, triacontanoic (or melissic) acid, dotriacontanoic (or lacceroic) acid, tetratriacontanoic (or gheddic) acid, pentatriacontanoic (or ceroplastic) acid, and the like; monoethenoic unsaturated fatty acids such as trans-2-butenoic (or crotonic) acid, cis-2-butenoic (or isocrotonoic) acid, 2-hexenoic (or isohydrosorbic) acid, 4-decanoic (or obtusilic) acid, 9-decanoic (or caproleic) acid, 4-dodecenoic (or linderic) acid, 5-dodecenoic (or denticetic) acid, 9-dodecenoic (or lauroleic) acid, 4-tetradecenoic (or tsuzuic) acid, 5-tetradecenoic (or physeteric) acid, 6-octadecenoic (or petroselenic) acid, trans-9-octadecenoic (or elaidic) acid, trans-11-octadecenoic (or vaccinic) acid, 9-eicosenoic (or gadoleic) acid, 11-eicosenoic (or gondoic) acid, 11-docosenoic (or cetoleic) acid, 13-decosenoic (or erucic) acid, 15-tetracosenoic (or nervonic) acid, 17-hexacosenoic (or ximenic) acid, 21-triacontenoic (or lumequeic) acid, and the like; dienoic unsaturated fatty acids such as 2,4-pentadienoic (or β-vinylacrylic) acid, 2,4-hexadienoic (or sorbic) acid, 2,4-decadienoic (or stillingic) acid, 2,4-dodecadienoic acid, 9,12-hexadecadienoic acid, cis-9, cis-12-octadecadienoic (or α-linoleic) acid, trans-9, trans-12-octadecadienoic (or linlolelaidic) acid, trans-10, trans-12-octadecadienoic acid, 11,14-eicosadienoic acid, 13,16-docosadienoic acid, 17,20-hexacosadienoic acid and the like; trienoic unsaturated fatty acids such as 6,10,14-hexadecatrienoic (or hiragonic) acid, 7,10,13-hexadecatrienoic acid, cis-6, cis-9-cis-12-octadecatrienoic (or γ-linoleic) acid, trans-8, trans-10-trans-12-octadecatrienoic (or β-calendic) acid, cis-8, trans-10-cis-12-octadecatrienoic acid, cis-9, cis-12-cis-15-octadecatrienoic (or α-linolenic) acid, trans-9, trans-12-trans-15-octadecatrienoic (or α-linolenelaidic) acid, cis-9, trans-11-trans-13-octadecatrienoic (or α-eleostearic) acid, trans-9, trans-11-trans-13-octadecatrienoic (or β-eleostearic) acid, cis-9, trans-11-cis-13-octadecatrienoic (or punicic) acid, 5,8,11-eicosatrienoic acid, 8,11,14-eicosatrienoic acid and the like; tetraenoic unsaturated fatty acids such as 4,8,11,14-hexadecatetraenoic acid, 6,9,12,15-hexadecatetraenoic acid, 4,8,12,15-octadecatetraenoic (or moroctic) acid, 6,9,12,15-octadecatetraenoic acid, 9,11,13,15-octadecatetraenoic (or α- or β-parinaric) acid, 9,12,15,18-octadecatetraenoic acid, 4,8,12,16-eicosatetraenoic acid, 6,10,14,18-eicosatetraenoic acid, 4,7,10,13-docasatetraenoic acid, 7,10,13,16-docosatetraenoic acid, 8,12,16,19-docosatetraenoic acid and the like; penta- and hexa-enoic unsaturated fatty acids such as 4,8,12,15,18-eicosapentaenoic (or timnodonic) acid, 4,7,10,13,16-docosapentaenoic acid, 4,8,12,15,19-docosapentaenoic (or clupanodonic) acid, 7,10,13,16,19-docosapentaenoic, 4,7,10,13,16,19-docosahexaenoic acid, 4,8,12,15,18,21-tetracosahexaenoic (or nisinic) acid and the like; branched-chain fatty acids such as 3-methylbutanoic (or isovaleric) acid, 8-methyldodecanoic acid, 10-methylundecanoic (or isolauric) acid, 11-methyldodecanoic (or isoundecylic) acid, 12-methyltridecanoic (or isomyristic) acid, 13-methyltetradecanoic (or isopentadecylic) acid, 14-methylpentadecanoic (or isopalmitic) acid, 15-methylhexadecanoic, 10-methylheptadecanoic acid, 16-methylheptadecanoic (or isostearic) acid, 18-methylnonadecanoic (or isoarachidic) acid, 20-methylheneicosanoic (or isobehenic) acid, 22-methyltricosanoic (or isolignoceric) acid, 24-methylpentacosanoic (or isocerotic) acid, 26-methylheptacosanoic (or isomonatonic) acid, 2,4,6-trimethyloctacosanoic (or mycoceranic or mycoserosic) acid, 2-methyl-cis-2-butenoic(angelic)acid, 2-methyl-trans-2-butenoic (or tiglic) acid, 4-methyl-3-pentenoic (or pyroterebic) acid and the like.

Compositions of the present invention also include active compounds (for example, finasteride) with alcohols having long alkyl chain. In some preferred embodiments, alcohols range from carbon chain lengths of about $C_5$ to $C_{34}$, preferably between about $C_4$ and about $C_{24}$. The alkyl chain in the present invention may be saturated or unsaturated.

In certain preferred embodiments, active compounds (for example, finasteride) comprise phospholipids. Any suitable phospholipids can be used. For example, phospholipids can be obtained from natural sources or chemically synthesized. Examples of phospholipids that find use in the present invention include phosphatidylethanolamine (PE), phosphatidylglycerol (PG), phosphatidylserine (PS), phosphatidylcholine (PC), phosphatidylinositol (PI), phosphatidic acid (PA), sphingomyelin and the like, either used separately or in combination. Phosphatidylglycerols may be having short chain or long chain, saturated or unsaturated such as dimyristoylphosphatidylglycerol, dioleoylphosphatidylglycerol, distearoylphosphatidylglycerol, dipalmitoylphosphatidylglycerol, diarachidonoylphosphatidylglycerol, short chain phosphatidylglycerol ($C_6$-$C_8$), and mixtures thereof. Examples of phosphatidylcholines includes dimyristoylphosphatidylcholine, distearoylphosphatidylcholine, dipalmitoylphosphatidylcholine, dioleoylphosphatidylcholine, diarachidonoylphosphatidylcholine, egg phosphatidylcholine, soy phosphatidylcholine or hydrogenated soy phosphatidylcholine can be used, as can mixtures thereof.

In some embodiments, the present invention provides compositions comprising at least one active compound (for example, finasteride) and derivatives of mono-, di- and tri-glycerides. Examples of the glycerides that find use in the present invention include but are not limited to 1-oleoyl glycerol (monoolein) and 1,2-dioctanoyl-sn-glycerol.

Another aspect of the invention is to provide a composition having at least one active compound (for example, finasteride) with at least one carbohydrate-based lipid. Examples of carbohydrate-based lipids that find use in the present invention include but are not limited to galactolipids, mannolipids, galactolecithin and the like.

Another aspect of the invention is to provide a composition comprising at least one active compound (for example, finsteride) with derivatives of phospholipids such as pegylated phospholipids. Examples include but not limited to the polyethylene glycol (Pegylated, PEG) derivatives of distearoylphosphatidylglycerol, dimyristoylphosphatidylglycerol, dioleoylphosphatidylglycerol and the like.

Another further aspect of the present invention provides compositions comprising at least one active compound (for example, finasteride) and polyethylene glycol (PEG) and one or more lipids.

According to another aspect, the present invention provides compositions comprising at least one active compound (for example, finasteride) and one or more lipids. Example includes compositions comprising finasteride, cholesterol or cholesterol derivatives and one or more phospholipids. Other examples of compositions according to the invention include finasteride, β-sitosterol, and one or more phospholipids. In some preferred embodiments, the composition of the present invention finasteride, cholesteryl sulfate and hydrogenated soy phosphatidylcholine or soy phosphatidylcholine.

According to another aspect, the present invention provides compositions comprising at least one active compound (for example, tacrolimus) and one or more lipids. Examples include compositions comprising tacrolimus, cholesterol or cholesterol derivatives and one or more phospholipids. Other examples of compositions according to the invention include finasteride, β-sitosterol, and one or more phospholipids. In some preferred embodiments, the composition of the present invention tacrolimus, cholesteryl sulfate and hydrogenated soy phosphatidylcholine or soy phosphatidylcholine.

According to another aspect, the present invention provides compositions comprising at least one active compound such as amphotericn B, and one or more lipids. Examples include compositions comprising amphotericn B, cholesterol or cholesterol derivatives and one or more phospholipids. Other examples of compositions according to the invention include amphotericin B, β-sitosterol, and one or more phospholipids. In some preferred embodiments, the composition of the present invention include amphotericin B, cholesteryl sulfate and hydrogenated soy phosphatidylcholine or soy phosphatidylcholine.

The composition of the present invention can be made by dissolving an active compound, for example, finasteride) in 70% isopropyl alcohol at a concentration of about 0.5 mg/mL to about 100 mg/mL. In some embodiments, the active compound is dissolved at a concentration between 1 mg/mL and about 50 mg/mL. In certain preferred embodiments, the active compound is dissolved at a concentration of between 1 mg/mL and 20 mg/mL. In particularly preferred embodiments, the active compound is dissolved at a concentration of between 1 mg/mL and 10 mg/mL.

In some embodiments, compositions of the present invention contain about 2.5% to about 95% by weight of total lipid, preferably about 10% to about 90% by weight of total lipid or more, preferably about 20% to about 90% by weight of total lipid.

In some embodiments, compositions of the present invention contain at least one active compound (for example, finasteride) and lipid(s) in mole ratio between 1:1 to 1:100, e.g., in between 1:1 and 1:20 molar ratio or in between 1:1 and 1:30 molar ratio or in between 1:1 and 1:40 molar ratio or in between 1:1 and 1:50 molar ratio, in between 1:1 and 1:60 molar ratio, in between 1:1 and 1:70 molar ratios, and in between 1:1 and 1:80 molar ratios. As used herein, the term "in between" is inclusive of the limits of a recited range. For example, a mole ratio "in between" 1:1 and 1:20 molar ratio includes ratios of 1:1 and 1:20.

In certain preferred embodiments, the mole ratio of active compound (for example, finasteride) and cholesteryl sulfate in a composition containing active compound (for example, finasteride), cholesteryl sulfate and hydrogenated soy phosphatidylcholine is in between 1:0.25 and 1:20, such as in between 1:0.5 and 1:10, or in between 1:1 and 1:5 or 1:1 and 1:2. In particularly preferred embodiments, the mole ratio of active compound (for example, finasteride) and cholesteryl sulfate is in between 1:0.5 and 1:5.

In certain preferred embodiments, the mole ratio of active compound (for example, finasteride) and guggul sulfate in a composition containing active compound (for example, finasteride), guggul sulfate and hydrogenated soy phosphatidylcholine is in between 1:0.25 and 1:20, such as in between 1:0.5 and 1:10, or in between 1:1 and 1:5 or 1:1 and 1:2. In particularly preferred embodiments, the mole ratio of active compound (for example, finasteride) and guggul sulfate is in between 1:0.5 and 1:5

In certain preferred embodiments, the mole ratio of active compound (for example, finasteride) and hydrogenated soy phosphatidylcholine in a composition containing active compound (for example, finasteride), cholesteryl sulfate and hydrogenated soy phosphatidylcholine is in between about 1:1 and 1:90, e.g., in between 1:1 and 1:70 or 1:1 and 1:60 or 1:1 and 1:50 or 1:1 and 1:40 and 1:1 and 1:30. In particularly preferred embodiments, the mole ratio of active compound (for example, finasteride) and hydrogenated soy phosphatidylcholine is in between 1:5 and 1:60.

In certain preferred embodiments, the mole ratio of active compound (for example, finasteride) and soy phosphatidylcholine in a composition containing active compound (for example, finasteride), cholesteryl sulfate and soy phosphatidylcholine is in between 1:1 and 1:90, e.g., in between 1:1 and 1:70 or 1:1 and 1:60 or 1:1 and 1:50 or 1:1 and 1:40 and 1:1 and 1:30. In particularly preferred embodiments, the mole ratio of active compound (for example, finasteride) and soy phosphatidylcholine is in between 1:5 and 1:60.

In certain preferred embodiments, the mole ratio of active compound (for example, finasteride) and soy phosphatidylcholine in a composition containing active compound (for example, finasteride), guggul sulfate and soy phosphatidylcholine is in between 1:1 and 1:90, e.g., in between 1:1 and 1:70 or 1:1 and 1:60 or 1:1 and 1:50 or 1:1 and 1:40 and 1:1 and 1:30. In particularly preferred embodiments, the mole ratio of active compound (for example, finasteride) and soy phosphatidylcholine is in between 1:5 and 1:60.

In some embodiments, compositions of the present invention contain active compound (for example, finasteride) and total lipids having weight-to-weight ratio between 1:1 to 1:100 ratio such as in between 1:1 and 1:20 ratio or in between 1:1 and 1:30 ratio or in between 1:1 and 1:40 ratio or in between 1:1 and 1:50 ratio, or in between 1:1 and 1:60 ratio, or in between 1:1 and 1:70 ratio, and in between 1:1 and 1:80 ratio, or in between 1:1 and 1:90 ratio.

In some embodiments, compositions of the present invention contain active compound (for example, finasteride) and soy phosphatidylcholine having weight-to-weight ratio between 1:1 to 1:100 ratio such as in between 1:1 and 1:20 ratio or in between 1:1 and 1:30 ratio or in between 1:1 and 1:40 ratio or in between 1:1 and 1:50 ratio, or in between 1:1 and 1:60 ratio, or in between 1:1 and 1:70 ratio, and in between 1:1 and 1:80 ratio, or in between 1:1 and 1:90 ratio.

In some embodiments, compositions of the present invention contain two active compounds (for example, finasteride and minoxidil) and soy phosphatidylcholine having weight-to-weight ratio between 1:1 to 1:100 ratio such as in between 1:1 and 1:20 ratio or in between 1:1 and 1:30 ratio or in between 1:1 and 1:40 ratio or in between 1:1 and 1:50 ratio, or in between 1:1 and 1:60 ratio, or in between 1:1 and 1:70 ratio, and in between 1:1 and 1:80 ratio, or in between 1:1 and 1:90 ratio.

In some embodiments, the methods of the present invention involve solubilizing active compound(s) for example, finasteride and lipid(s), in water or suitable buffer. The active compound-lipid complex solution can be filtered through suitable filters to control the size distribution of the formed complexes.

In some embodiments, the methods of the present invention involve dissolving active compound, e.g., finasteride, in non-toxic solvent and mixing the dissolved active compound and the lipid(s) together. The non-toxic solvent in the present invention include but not limited to ethanol, 1-propanol, isopropanol, propylene glycol, and 1-butanol. The percentage of the non-toxic solvent in the present invention ranges between 100% and 10% such as in between 80% and 20%, such as in between 60% and 40%. In preferred embodiment the percentage of non-toxic solvent ranges between 80% and 50%.

In some embodiments, the methods of the present invention involve dissolving active compound, e.g., finasteride, in non-toxic solvent-water system and mixing the dissolved active compound and the lipid(s) together. The non-toxic solvent in non-toxic solvent-water system in the present invention includes but not limited to ethanol, 1-propanol, isopropanol, propylene glycol, and 1-butanol. The percentage of the non-toxic solvent in the present invention ranges between 100% and 10% such as in between 80% and 20%, such as in between 60% and 40%. In preferred embodiment the percentage of non-toxic solvent ranges between 80% and 50%.

In some embodiment, the methods of the present invention involve dissolving active compound(s) e.g. finasteride and/or minoxidil and lipid(s) together in more than one non-toxic solvents and water. For example, finasteride and or monoxidil can be dissolved in isopropyl alcohol-propylene glycol-water system. The percentage of the total non-toxic solvent in the present invention ranges between 90% and 10% such as in between 80% and 20%, such as in between 60% and 40%. In preferred embodiment the percentage of non-toxic solvent ranges between 80% and 50%.

In some embodiments, the methods of the present invention involve mixing active compound and lipid (s) for example, finasteride and soy phosphatidylcholine in isopropyl alcohol-water solution until the solution is completely clear. The percentage of isopropyl alcohol in isopropyl-water solution ranges between 10 and 90 percent such as in between 40 and 80 percent, such as in between 50 and 70 percent.

In some embodiments, the methods of the present invention involve mixing active compound and lipid (s) for example, finasteride and soy phosphatidylcholine in ethanol-water solution until the solution is completely clear. The percentage of ethanol in isopropyl-water solution ranges between 10 and 90 percent such as in between 40 and 80 percent, such as in between 50 and 70 percent In some embodiments, the compositions of present invention involve more than one active compound and one more lipids. For example, the composition contains finasteride as one active agent and minoxidil as second active agent. The mole ratio of one active agent to another active agent in the present invention ranges in between 1:0.5 to 1:100, e.g., in between 1:1 and 1:20 molar ratio or in between 1:1 and 1:30 molar ratio or in between 1:1 and 1:40 molar ratio or in between 1:1 and 1:50 molar ratio, in between 1:1 and 1:60 molar ratio, in between 1:1 and 1:70 molar ratios, and in between 1:1 and 1:80 molar ratios. As used herein, the term "in between" is inclusive of the limits of a recited range. For example, a mole ratio "in between" 1:1 and 1:20 molar ratio includes ratios of 1:1 and 1:20.

In some embodiments, the methods of the present invention involve mixing active compound(s) (for example, finasteride and minoxidil) and lipid(s) for example, soy phosphatidylcholine in isopropyl alcohol-water solution until the solution is completely clear. The percentage of isopropyl alcohol in isopropyl-water solution ranges between 30 and 90 percent such as in between 40 and 80 percent, such as in between 50 and 70 percent.

In some embodiments, the methods of the present invention involve mixing active compound(s) (for example, finasteride and/or minoxidil) and lipid(s) for example, soy phosphatidylcholine in ethanol-water solution until the solution is completely clear. The percentage ethanol in ethanol-water solution ranges between 30 and 90 percent such as in between 40 and 80 percent, such as in between 50 and 70 percent.

In some embodiments, the methods of the present invention involve mixing active compound(s) (for example, finasteride and/or minoxidil) and lipid(s) for example, soy phosphatidylcholine in ethanol-water solution containing polysorbate 80 until the solution is completely clear. The percentage of ethanol in ethanol-water solution ranges between 30 and 90 percent such as in between 40 and 80 percent, such as in between 50 and 70%. The percentage of polysorbate 80 in ethanol-water mixture ranges between 10 and 60 percent such as in between 20 and 50 percent such as in between 25 and 40 percent.

In some embodiments, the methods of the present invention involve mixing active compound(s) (for example, finasteride and/or minoxidil) and lipid(s) for example, soy phosphatidylcholine in isopropyl alcohol-water solution containing polysorbate 80 until the solution is completely clear. The percentage of isopropyl alcohol in isopropyl-water solution ranges between 30 and 90 percent such as in between 40 and 80 percent, such as in between 50 and 70 percent. The percentage of polysorbate 80 in ethanol-water mixture ranges between 10 and 60 percent such as in between 20 and 50 percent such as in between 25 and 40 percent In some embodiments, the methods of the present invention involve mixing active compound(s) (for example, finasteride and/or minoxidil) and lipid(s) for example, soy phosphatidylcholine in oleyl alcohol until the solution is clear.

In some embodiment, the methods of present invention involve mixing active compound(s), (for example, finasteride and/or minoxidil) and lipid(s) for example, soy phosphatidylcholine in propylene glycol and homogenize or sonicate until the solution is completely clear.

In some embodiments, the methods of the present invention involve mixing active compound(s) (for example, finasteride and/or minoxidil) and lipid(s) for example, soy phosphatidylcholine in propylene glycol-isopropyl alcohol-water solution until the solution is completely clear. The percentage of isopropyl alcohol in propylene glycol-isopropyl alcohol-water solution ranges between 10 and 90 percent such as in between 30 and 80 percent, such as in between 40 and 70 percent. The percentage of propylene glycol in propylene glycol-isopropyl alcohol-water solution ranges between 10 and 80 percent such as in between 20 and 60 percent such as in between 25 and 50 percent.

In some embodiments, the methods of the present invention involve mixing active compound(s) (for example, finasteride and/or minoxidil) and lipid(s) for example, soy phosphatidylcholine in propylene glycol-ethanol-water solution until the solution is completely clear. The percentage of ethanol in propylene glycol-ethanol-water solution ranges between 10 and 90 percent such as in between 30 and 80 percent, such as in between 40 and 70 percent. The percentage of propylene glycol in propylene glycol-ethanol-water solution ranges between 10 and 80 percent such as in between 20 and 60 percent such as in between 25 and 50 percent.

In some embodiments, the methods of the present invention involve mixing active compound(s) (for example, finasteride and/or minoxidil) and lipid(s) for example, soy phosphatidylcholine in suitable oil and homogenize or sonicate until it is completely clear. Examples of suitable oil includes but not limited to vegetable oil, such as olive oil, castor oil, saff flower oil, sunflower oil, canola oil, soybean oil, peanut oil, coconut oil, sesame seed oil, almond oil.

In some embodiments, compositions of the present invention having more than one active agent, (for example, finasteride and minoxidil), the weight-to-weight ratio of one active agent and the second active agent is in between 1:0.5 to 1:100 ratio such as in between 1:1 and 1:20 ratio or in between 1:1 and 1:30 ratio or in between 1:1 and 1:40 ratio or in between 1:1 and 1:50 ratio, or in between 1:1 and 1:60 ratio, or in between 1:1 and 1:70 ratio, and in between 1:1 and 1:80 ratio, or in between 1:1 and 1:90 ratio.

In some embodiments, the method of the present invention involves mixing lipid(s) and active compound(s) together in non-toxic solvent. The active compound-lipid composition solution can be filtered through suitable filters to control the size distribution of the formed complexes.

In some embodiments, the method of preparation of present invention comprising mixing active compound (for example, finasteride), cholesteryl derivative (for example, cholesteryl sulfate) and phosphatidylcholine such as soy phosphatidylcholine or hydrogenated soy phosphatidylcholine in water or buffer. The resulting suspension can be homogenized or sonicated at any desired temperature ranging from 20-60° C. Examples of base or buffer includes but not limited to sodium succinate dibasic, sodium acetate, sodium phosphate monobasic, sodium phosphate dibasic, sodium phosphate tribasic, sodium citrate, sodium hydroxide, and the like. The resulting suspension can be homogenized or sonicated to reduce the particle size. In some embodiments, the hydrated suspension is filtered through suitable filters to control the size distribution of the formed complexes. In some composition, the hydrated suspension can be lyophilized to obtain the composition in powder form. In some embodiments, the hydrated composition can be autoclaved. In some embodiments, a cryoprotectant such as sugars may be added to facilitate lyophiliztion. Examples of sugars include but not limited to trehalose, dextrose, sucrose, lactose, maltose, and the like. The percentage of sugar may range from 5% to about 25%.

In some embodiments, a method of preparation of the present invention comprising mixing one or more active compounds (e.g., tacrolimus or amphotericin B), a cholesterol derivative (e.g., cholesteryl sulfate) and a phosphatidyl choline such as soy phosphatidylcholine or hydrogenated soy phosphatidylcholine in ethanol or isopropanol. The resulting solution or suspension can be mixed with suitable base used commonly used is ointments and sprays.

In some embodiments, the composition of the present invention can be sterilized by filtering through 0.22 μm or 0.45 μm filter under aseptic conditions. In other embodiments, the composition of the present invention can be sterilized by autoclaving in the range of 110° C.-130° C. for duration of 15-20 minutes.

Pharmaceutical preparations that find use in the present invention include but are not limited to solutions, suspensions, emulsions, ointments; suppositories, gels can be suitable pharmaceutical preparations. In some embodiments, e.g., for topical application and suppositories, active compound-lipid composition (for example, finasteride-lipid composition) is provided in the form of solutions, gels, oils, and emulsions, such as are known by the addition of suitable water-soluble or water-insoluble excipients, for example polyethylene glycols, certain fats, and esters, compounds having a higher content of polyunsaturated fatty acids and derivatives thereof. Derivatives include but are not limited to mono-, di-, and triglycerides and their aliphatic esters (for example, fish oils, vegetable oils etc.) or mixtures of these substances. In some embodiments, excipients that find use in conjunction with the compositions of the present invention comprise those in which the drug complexes are sufficiently stable to allow for therapeutic use. In some embodiments, the oral mode of administration, the composition of present invention is used in the form of tablets, capsules, lozenges, powders, syrups, aqueous solutions, suspensions, and the like.

In some embodiments, the composition of the present invention can be admixed with other carrier substances known in the art. Examples of carrier substances include but not limited to glycerine, oils, mineral oil, propylene glycol, alcohol, aloe vera gel, allantoin, vitamin A and E, PPG2 myristyl propionate, and the like. The said mixture of composition and carrier substance can be administered topically in the form of solutions, creams, gels, lotions, shampoo, paste (See, e.g., Rasmusson et al., EP 0285 382, 1988).

Preparations of active compound-lipid composition (for example, finasteride-lipid composition) of the present invention can comprise composition of varying size, or can comprise composition of substantially uniform size. For example, in some embodiments the composition have a size range of about 1 mm or less, while in preferred embodiments, the composition are in the micron or sub-micron range. In some embodiments, the composition have a diameter of about 5 μm or less, such as 0.2 μm or less, or even 01. μm or less.

Active compound-lipid composition (for example, finasteride-lipid composition) of the present invention may comprise or consist essentially of micelles, mixed micelles, liposomes and vesicles of different shape and sizes.

As noted above, the technology outlined in the present invention for the preparation of finasteride composition is also suitable for use with any other water-insoluble drugs.

The composition of present invention can be employed (for example, finasteride-lipid composition or finasteride-minoxidil-lipid composition) to treat androgenic alopecia and promoting hair growth in males. In some embodiments, the composition of present invention can also be employed in preventing hair loss in males. In some embodiments, the composition of present invention can also be employed to treat hirsutism in females. In some embodiments, the composition of present invention can also be used to treat acne vulgaris and seborrhea.

The composition of present invention (for example, finasteride-lipid composition) can also be employed to treat benign prostatic hyperplasia in males.

The examples of the present invention are illustrated below but the invention is not limited to the following examples and modifications can be made without departing from the purports described in this application.

Example I

Finasteride (100 mg) and Soya Phosphatidylcholine (4 g) was blended together in sodium citrate, monobasic (100 mL) and then subjected to high pressure homogenization. The particle size was determined using Nicomp Particle Sizer 380. The mean volume diameter amounted to less than 200 nm.

Example II

Finasteride (100 mg), sodium cholesteryl sulfate (66 mg) and Soya Phosphatidylcholine (3.94 g) was blended together in sodium citrate, monobasic (100 mL) and then subjected to high pressure homogenization. The particle size was determined using Nicomp Particle Sizer 380. The mean volume diameter amounted to less than 200 nm.

Example III

Finasteride (10 mg) and Soya Phosphatidylcholine (25 mg) was mixed together in soybean oil (2 mL) and sonicated for 40 minutes.

Example IV

Finasteride (200 mg) and Soy phosphatidylcholine (1 g) was mixed together in 70% isopropyl alcohol (40 mL) and sonicated until a solution is formed.

Example V

Finasteride (10 mg), soy phosphatidylcholine (50 mg), and polysorbate 80 (0.5 mL) was solubilized in ethanol (0.5 mL) and water (1 mL) was added and stirred vigorously.

Example VI

Finasteride (10 mg), soy phosphatidylcholine (50 mg), and polysorbate 80 (0.5 mL) was solubilized in ethanol (0.5 mL) and water (1 mL) was added and stirred vigorously.

Example VII

Finasteride (10 mg) and soy phosphatidylcholine (50 mg) was solublized in isopropyl alcohol (0.5 mL) and water (0.5 mL) was added and stirred vigorously.

Example VIII

Finasteride (10 mg) and soy phosphatidylcholine (50 mg) was solublized in isopropyl alcohol (2.5 mL) and water (2.5 mL) was added and stirred vigorously.

Example VIII

Finasteride (2 mg) and soy phosphatidylcholine (10 mg) was solubilized in 70% isopropyl alcohol in water (1 mL) and added to a suspension of Minoxidil (50 mg) in 60% propylene glycol in water (1 mL). The suspension was homogenized or sonicated until the solution is clear.

Example IX

Finasteride (2 mg) and soy phosphatidylcholine (20 mg) was solubilized in 70% isopropyl alcohol in water (1 mL) and added to a suspension of Minoxidil (80 mg) in 60% propylene glycol in water (1 mL). The suspension was homogenized or sonicated until the solution is clear.

Example X

Finasteride (2 mg), Minoxidil (100 mg) and soy phosphatidylcholine (20 mg) was solubilized in propylene glycol (2 mL).

Example XI

Finasteride (2 mg), Minoxidil (100 mg) and soy phosphatidylcholine (20 mg) was solubilized in a solution containing isopropyl alcohol (0.7 mL), propylene glycol (0.6 mL) and water (0.6 mL).

Example XII

Finasteride (2 mg), Minoxidil (100 mg) and soy phosphatidylcholine (20 mg) was solubilized in a solution containing isopropyl alcohol (0.0.32 mL), propylene glycol (1.2 mL) and water (0.48 mL).

Example XIII

Finasteride (2 mg), Minoxidil (100 mg) and soy phosphatidylcholine (20 mg) was solubilized in a solution containing isopropyl alcohol (1.2 mL), propylene glycol (0.4 mL) and water (0.4 mL).

Example XIV

Finasteride (2 mg), Minoxidil (100 mg) and soy phosphatidylcholine (20 mg) was solubilized in a solution containing isopropyl alcohol (0.8 mL), propylene glycol (0.6 mL) and water (0.6 mL).

Example XIV

Finasteride (2 mg), Minoxidil (100 mg) and soy phosphatidylcholine (20 mg) was solubilized in a solution containing isopropyl alcohol (0.8 mL), propylene glycol (0.6 mL) and water (0.6 mL).

Example XV

Finasteride (20 mg), Minoxidil (1 g) and soy phosphatidylcholine (20 mg) was solubilized in a solution containing isopropyl alcohol (0.4 mL), propylene glycol (1.2 mL) and water (0.4 mL).

Example XVI

Finasteride (20 mg) and Minoxidil (1 g) and soy phosphatidylcholine (200 mg) was taken in propylene glycol (20 mL) and homogenized or sonicated until all ingredients are completely soluble.

Example XVII

Finasteride (20 mg) and Minoxidil (1 g) and soy phosphatidylcholine (200 mg) was taken in propylene glycol (20 mL) and homogenized or sonicated until the solution is completely clear.

Example XVIII

Finasteride (40 mg) and Minoxidil (2 g) and soy phosphatidylcholine (200 mg) was taken in isopropanol:propylene glycol:water (50:30:20, 40 mL) and homogenized or sonicated until the solution is completely clear.

Example XIX

Finasteride (40 mg) and Minoxidil (2 g) and soy phosphatidylcholine (400 mg) was taken in isopropanol:propylene glycol:water (50:30:20, 40 mL) and homogenized or sonicated until the solution is completely clear.

Example XX

Finasteride (40 mg) and Minoxidil (2 g) and soy phosphatidylcholine (200 mg) was taken in isopropanol:propylene glycol:water (50:40:10, 40 mL) and homogenized or sonicated until the solution is completely clear.

Example XXI

Finasteride (40 mg) and Minoxidil (2 g) and soy phosphatidylcholine (400 mg) was taken in isopropanol:propylene glycol:water (50:40:10, 40 mL) and homogenized or sonicated until the solution is completely clear.

Example XXII

Finasteride (40 mg) and Minoxidil (2 g) and soy phosphatidylcholine (200 mg) was taken in isopropanol:propylene glycol:water (40:50:10, 40 mL) and homogenized or sonicated until the solution is completely clear.

Example XXIII

Finasteride (40 mg) and Minoxidil (2 g) and soy phosphatidylcholine (400 mg) was taken in isopropanol:propylene glycol:water (40:50:10, 40 mL) and homogenized or sonicated until the solution is completely clear.

Example XXIV

Tacrolimus (20 mg) and soy phosphatidylcholine (200 mg) was taken in isopropanol and homogenized or sonicated until the solution is completely clear.

REFERENCES

1. Deray G.; Mercadal, L.; Bagnis, C. *Nephrologie*, 2002, 23, 119-122.
2. Gormley, G. J., Kauffmann, K. D., Stoner, E., Waldstreicher, J. U.S. Pat. No 5,981,543, 1999.
3. Hammarstrom, L.; and Smith, C. I. E. *Acta Patho. Microbial. Scand.* 1977, 85, 277-283.
4. Roberts, J. *Dermatology Nursing*, 1977, 9, 379-386
5. Roberts, J. *J. Amer. Acad. Derm.*, 1987, 16, 705-710.
6. Medoff, G. and Kobayashi, G. S. *J. Am. Med. Assoc.* 1975, 232, 619-620.
7. Niemiee, S. M., Wang, J. C. T., Wisniewski, S. J., Stenn, K. S., Lu, G. W. U.S. Pat. No. 6,419,913 B1, 2002
8. Olsen, E. A., Weiner, M. S., DeLong, E. R., Pinnell, S. *J. Amer. Acad. Derm.*, 1985, 13, 185-192.
9. Rasmusson, G. H., Johnston, D. B. R., Arth, G. E. U.S. Pat. No. 4,377,584, 1983.
10. Rasmusson, G. H., Reynolds, G. F. EP Patent No. 0285382B1, 1988
11. Valeriote, F.; Lynch, R.; Medoff, G.; and Kumar, B. V. *J. Natl. Cancer. Inst.* 1976, 56, 557-559.

All references, including publications, patent applications, and patent cited herein, including those in the preceding list and otherwise cited in this specification, are hereby incorporated by reference to the same extent as if each reference was individually and specifically indicated to be incorporated by reference and were set forth in the entirely herein.

Preferred embodiments of this invention are described, including the best mode known to the inventors for carrying out the invention. Various modifications and variations of the described methods and systems of the invention will be apparent to those skilled in the art without departing from the scope and spirit of the invention, and the inventors intend for the inventions to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Indeed, any modifications of the described modes for carrying out the invention that are obvious to those skilled in the relevant fields are intended to be within the scope of the following claims.

What is claimed is:

1. A lipid composition comprising at least two active compounds dissolved in a non-toxic solvent-water system, wherein the composition comprises:
    effective amounts of finasteride and minoxidil; and
    a lipid or mixture of lipids
    in a non-toxic solvent-water system, wherein the composition is a clear lipidic solution obtainable by mixing dissolved active compound and a lipid or mixture of lipids together in said non-toxic solvent-water system to produce said clear lipid solution.

2. The lipid composition of claim 1, wherein said lipid or mixture of lipids is selected from the group consisting of egg phosphatidylcholine (EPC), egg phosphatidylglycerol (EPG), soy phosphatidylcholine (SPC), hydrogenated soy phosphatidylcholine (HSPC), dimyristoylphosphatidylcholine (DMPC), dimyristoylphosphatidylglycerol (DMPG), dipalmitoylphosohatidylcholine (DPPC), disteroylphosphatidylglycerol (DSPG), dipalmitoylphosphatidylglycerol (DMPG), phosphatidylethanolamines, phosphatidylserine, phosphatidylinositol, phosphatidic acid, cholesterol (Chol), cholesterol sulfate and its salts (CS), cholesterol hemisuccinate and its salts (Chems), cholesterol phosphate and its salts (CP), cholesterylphosphocholine, hydroxycholesterol derivatives, amino cholesterol derivatives, cholesteryl succinate, cholesteryl oleate, polyethylene glycol derivatives of cholesterol (cholesterol-PEG), coprostanol, cholestanol, cholestane, cholic acid, cortisol, corticosterone, hydrocortisone, and calciferol; guggulsterol, guggul sulfate and its salts, guggul laurate, guggulsterol derivatives containing long chain or short chain, saturated or unsaturated fatty acids, gugguloleate, guggul myristate, monoglycerides, diglycerides, triglycerides, carbohydrate-based lipids selected from a group consisting of galactolipid, mannolipid, galactolecithin, fatty acids selected from a group consisting of saturated or unsaturated fatty acids having a chain length of $C_4$-$C_{34}$, long chain alcohols selected from a group consisting of saturated or unsaturated alcohols having a chain length of $C_5$-$C_{34}$, and pegylated derivatives of a phospholipid selected from the group consisting of pegylated derivatives of distearoylphosphatidylglycerol, dipalmitoylphosphatidylglycerol, dimyristoylphosphatidylglycerol, and dioleoylphosphatidylglycerol.

3. The lipid composition of claim 1, wherein the composition further comprises polyethylene glycol (PEG) having an average molecular weight ranging from about 200-20, 000.

4. The lipid composition of claim 1, further comprising an active compound selected from the group consisting of Duasteride, Amphotericin B, and Tacrolimus.

5. The lipid composition of claim 1, wherein the non-toxic solvent-water system comprises at least one alcohol, said alcohol selected from the group consisting of ethanol, propyl alcohol, isopropyl alcohol, propylene glycol, and butanol.

6. The lipid composition of claim 1, wherein the non-toxic solvent-water system comprises at least one oil selected from the group consisting of soybean oil, vegetable oil, olive oil, coconut oil, sunflower oil, almond oil, canola oil, sesame seed oil, peanut oil, corn oil, and cod oil.

7. The lipid composition of claim 1, wherein said composition in a suitable vehicle for administration, wherein said vehicle is water or aqueous buffer comprising one or more non-toxic solvents selected from a group consisting of ethanol, propyl alcohol, isopropyl alcohol, propylene glycol, and butanol.

8. The lipid composition of claim 1, wherein said composition comprises finasteride, minoxidil, soy phosphatidylcholine and 70% isopropyl alcohol in water.

9. The lipid composition of claim 1, wherein said composition comprises finasteride, minoxidil, and soy phosphatidylcholine in propylene glycol.

10. The lipid composition of claim 1, wherein said composition comprises finasteride, minoxidil, and soy phosphatidylcholine in propylene glycol-isopropyl alcohol-water solution.

11. The lipid composition of claim 1, wherein said composition comprises tacrolimus, cholesteryl sulfate, and soy phosphatidylcholine in isopropanol or ethanol.

12. The lipid composition of claim 1, wherein said composition comprises amphotericin B, cholesteryl sulfate, and soy phosphatidylcholine in isopropanol or ethanol.

\* \* \* \* \*